United States Patent [19]

Milligan

[11] 3,984,488

[45] Oct. 5, 1976

[54] DINITRATION OF NITROBENZOTRIFLUORIDE

[75] Inventor: Barton Milligan, Ardmore, Pa.

[73] Assignee: Air Products and Chemicals, Inc., Allentown, Pa.

[22] Filed: May 23, 1975

[21] Appl. No.: 580,505

[52] U.S. Cl. ............................................. 260/646
[51] Int. Cl.$^2$ ........................................ C07C 79/12
[58] Field of Search ................................... 260/646

[56] References Cited
UNITED STATES PATENTS 2,257,093  9/1941  Friedrich et al. ................... 260/646

*Primary Examiner*—Leland A. Sebastian
*Attorney, Agent, or Firm*—Russell L. Brewer; Barry Moyerman

[57] ABSTRACT

This invention relates to an improvement in an process for dinitrating 3-nitrobenzotrifluoride and 4-halo-3-nitrobenzotrifluoride compounds wherein the mononitrobenzotrifluoride composition is contacted with a mixture comprising sulfuric and nitric acid. The improvement constituting the basis of this invention comprises carrying out the dinitration with the sulfuric acid being present in at least a catalytic proportion but not exceeding about 65 mole percent in said mixture.

7 Claims, No Drawings

DINITRATION OF NITROBENZOTRIFLUORIDE

BACKGROUND OF THE INVENTION

The dinitration of 4-halo-3-nitrobenzotrifluoride and 3-nitrobenzotrifluoride compounds has been practiced for some time. As is known, it is particularly difficult to achieve nitration of these compositions because of the deactivation of the aromatic ring by the trifluoromethane radical, and nitro group. The ring is deactivated further in the first instance by the halo group thereby making these compounds one of the most difficult to nitrate.

In spite of the nitration difficulties commercially acceptable procedures have been sought because of the extreme importance of these compositions as intermediates for the preparation of herbicides. As is known one of these compounds can be converted to trifluralin.

DESCRIPTION OF THE PRIOR ART

It has been proposed to dinitrate 4-chloro-3-nitrobenzotrifluoride with a mixture of nitric acid and concentrated sulfuric acid at low temperatures e.g., below about 90° C. One of the basic problems with this procedure is that reaction times were extremely long e.g., several days. Even though dinitration took several days, there was a corresponding problem associated with the nitration in that the trifluoromethane group hydrolyzed under these conditions thereby resulting in reduced product.

That process was improved upon by carrying out the dinitration reaction at elevated temperatures e.g., 200° C and above in the presence of a mixture comprising sulfuric acid containing an excess of sulfur trioxide and an alkali metal nitrate in which the mole ratio of excess sulfur trioxide to nitrate ions was from about 1.5:1 to 2.0:1. This process resulted in good yields e.g., 80 percent and above and short reaction times e.g., about an hour. However, the spent sulfuric acid could not be regenerated to the desired concentration and thereby made the process expensive.

SUMMARY OF THE INVENTION

This invention relates to an improvement in a process for dinitrating 3-nitrobenzotrifluoride and 4-halo-3-nitrobenzotrifluoride compounds by contacting the nitrobenzotrifluoride with a mixture comprising nitric acid and sulfuric acid under conditions for effecting dinitration. The improvement comprises carrying out said dinitration with a mixture in which the sulfuric acid is present in at least a catalytic amount but not in a concentration exceeding about 65 mole percent based on the mixture.

Advantages of this process over those in the prior art include:
the ability to effect dinitration of an extremely difficult compound with good yield;
the ability to effect dinitration without the use of oleum thereby eliminating many of the handling problems associated with the nitration mediums in the past;
the ability to effect dinitration with a sulfuric acid composition which can be obtained from a nitration process by conventional regeneration thereby enhancing economics; and
the ability to effect dinitration with a minimum amount of hydrolysis of the trifluoromethane radical.

DESCRIPTION OF THE PREFERRED EMBODIMENTS

Compositions suited for practicing this invention are the 3-nitrobenzotrifluorides and 4-halo-3-nitrobenzotrifluorides. With respect to the halobenzotrifluorides, the halo groups can be any of the halogen atoms but preferably chlorine is the preferred halogen atom for herbicidal synthesis.

It has been found that both the 3-nitrobenzotrifluoride and 4-halo-3-nitrobenzotrifluoride composition and particularly 4-chloro-3-nitrobenzotrifluoride is stable to hydrolysis under nitration conditions when the sulfuric acid is present in a concentration below about 65 mole percent. When the concentration of sulfuric acid exceeds about 65 mole percent, the rate of hydrolysis of the nitrobenzotrifluoride increases rapidly. In other words, the rate of nitration is much faster than the rate of hydrolysis at nitration conditions when the sulfuric acid is present in less than 65 mole percent. Thus if the concentration of sulfuric acid exceeds about 65 mole percent in the nitration reaction, e.g., 70 percent, the rate of the competing hydrolysis reaction increases substantially and thereby reduces the amount of product. On the other hand, if the nitration is carried out with mixture containing less than 65 mole percent and preferably from 50 to 60 mole percent sulfuric acid, the rate of hydrolysis of the nitrobenzotrifluoride is negligible compared to the rate of dinitration.

The dinitration reaction should be carried out at a temperature of from about 40° to 150° C. Preferably the temperature for dinitration is from 90° to 110° C. as the 3-nitrobenzotrifluoride and 4-halo-3-nitrobenzotrifluoride compositions are quite stable to hydrolysis at this temperature. For example, the half life of 4-chloro-3-nitrobenzotrifluoride at 100° C. in a mixture containing 60 mole percent sulfuric acid is about 5 hours. The corresponding dinitrochlorobenzotrifluoride has a half life greater than 24 hours. Thus, at these temperatures it is possible to achieve a rate of nitration sufficient for generating the more stable dinitrobenzotrifluoride and dinitrohalobenzotrifluoride in good yield.

Nitration of the 3-nitro-4-benzotrifluoride and 4-halo-3-nitrobenzotrifluorides is carried out by contacting the nitrobenzotrifluorides with a material capable of generating nitronium ions. Generally, most nitration reations are carried out by employing nitric acid as the nitrating agent. However, it is known that nitric acid can be generated in situ to minimize the amount of water present in a nitration medium by employing an alkali-metal nitrate and converting this nitrate to nitric acid by contacting it with an acid e.g., sulfuric.

The following examples are provided to illustrate preferred embodiments of the invention and are not intended to restrict the scope thereof.

EXAMPLE I

The preparation of 4-chloro-3, 5-dinitrobenzotrifluoride is effected by first forming a mixture containing 3.04 moles nitric acid, 6.55 moles sulfuric acid and 1.18 moles water. The mixture is prepared by mixing white fuming nitric acid (approximately 90 percent nitric acid) with 100 percent sulfuric acid. This mixture is charged to a 1 liter Morton flask containing 1.01 moles of 3-nitro-4-chlorobenzotrifluoride. The reaction is carried out by agitating with a turbine type stirrer rotated at 1,000 rpm and at a temperature of about 110° C. for 14 hours. At the end of a 14 hour period, the reaction medium is cooled to about 60° and the acid and organic phases separated. The organic phase is washed with water to remove any water-soluble salts and acids therein. A small amount of 4-chloro-3, 5-dinitrobenzotrifluoride is recovered from the spent acid by extracting with chloroform.

Thin layer chromotography shows that about 3 to 4 percent of 4-chloro-3, 5-dinitrobenzoic acid is present in the product. These results show that very little hydrolysis of the product occurrs during the nitration reaction thus showing the stability of the nitrobenzotrifluoride in a nitrating mixture containing approximately 60 hole percent sulfuric acid. The yield of the desired dinitrobenzenetrifluoride product is about 88 percent of the theoretical based on the 4-chloro-3-nitrobenzotrifluoride charged.

EXAMPLE II

A 4-chloro-3, 5-dinitrobenzotrifluoride product is prepared by adding 1 mole of 4-chloro-3-nitrobenzotrifluoride to a nitrating mixture containing 3.04 moles nitric acid, 10.13 moles sulfuric acid, (59.9 mole percent sulfuric acid) and 3.72 moles water based on the mixture formed by mixing 94 percent (by weight) sulfuric acid in water obtained from a reconcentration process for sulfuric acid with 98 percent (by weight) nitric acid.

The nitration reaction is carried out at about 110° C. with vigorous agitation. The 4-chloro-3-nitrobenzotrifluoride is added to the mixture over a period of about 2 hours and the reaction is permitted to continue for 12 hours with additional heating. At the end of a 12 hour period, the mixture is cooled and the organic layer containing the desired 4-chloro-3, 5-dinitrobenzotrifluoride is separated and washed with water. The yield of product, based on the organic material charged is good and there is very little dinitrobenzoic acid present in the mixture showing that hydrolysis is kept to a very low level.

EXAMPLE III

The nitration of 4-chloro-3-nitrobenzotrifluoride is carried out by first forming a mixture containing 1.01 moles 4-chloro-3-nitrobenzotrifluoride, 6.55 moles sulfuric acid, and 1.96 moles water. The sulfuric acid present in this mixture is about 77 mole percent. The mixture is heated, and at a temperature of about 100° C. rapid evolution of gas is noticed. During this period the organic layer completely dissolves in the acid layer and gas evolution continues for about 1½ hours at which time effervescence subsides. Nitric acid is added to the mixture in an amount sufficient to bring the sulfuric acid content to about 60 mole percent and the mixture is heated for an additional hour. On cooling 4-chloro-3, 5-dinitrobenzoic acid is obtained.

This example shows that substantial hydrolysis of the mononitrobenzotrifluoride composition occurs with the sulfuric acid concentration is about 77 mole percent. On the other hand, the previous example shows that excellent yields in terms of dinitrated product can be obtained, with minimum hydrolysis when the sulfuric acid concentration does not exceed about 65 percent.

What is claimed is:

1. A process for dinitrating a nitrobenzotrifluoride composition selected from the group consisting of 3-nitrobenzotrifluoride and 4-halo, 3-nitrobenzotrifluoride which comprises contacting the nitrobenzotrifluoride composition under dinitrating conditions with a mixture comprising water, nitric acid, and at least a catalytic amount but not an amount exceeding about 65 mol % of the mixture of sulfuric acid.

2. The process of claim 1 wherein said nitrobenzotrifluoride is 4-chloro-3-nitrobenzotrifluoride.

3. The process of claim 2 wherein said nitration temperature is from about 40° to 150° C.

4. The process of claim 3 wherein said sulfuric acid is present in a proportion of from about 50 to 60 mole percent in said mixture.

5. The process of claim 1 wherein said nitrobenzotrifluoride is 3-nitrobenzotrifluoride.

6. The process of claim 5 wherein said nitration temperature is from about 50° to 120° C.

7. The process of claim 6 wherein said sulfuric acid is present in a proportion of from about 50 to 60 mole percent in said mixture.

* * * * *